(12) United States Patent
Moskalenko

(10) Patent No.: US 8,207,731 B2
(45) Date of Patent: Jun. 26, 2012

(54) APPARATUS AND METHOD FOR AUTOMATIC PRODUCT EFFECT COMPENSATION IN RADIO FREQUENCY METAL DETECTORS

(75) Inventor: Sergey A. Moskalenko, Maple Grove, MN (US)

(73) Assignee: Thermofisher Scientific, Coon Rapids, MN (US)

( * ) Notice: Subject to any disclaimer, the term of this patent is extended or adjusted under 35 U.S.C. 154(b) by 482 days.

(21) Appl. No.: 12/587,083

(22) Filed: Sep. 30, 2009

(65) Prior Publication Data

US 2011/0074401 A1    Mar. 31, 2011

(51) Int. Cl.
*G01R 33/12* (2006.01)
(52) U.S. Cl. ........................................ 324/233
(58) Field of Classification Search .................. 324/233
See application file for complete search history.

(56) References Cited

U.S. PATENT DOCUMENTS

| 4,719,421 A | | 1/1988 | Kerr | |
|---|---|---|---|---|
| 5,045,789 A | | 9/1991 | Inoue et al. | |
| 5,189,366 A | * | 2/1993 | Mayo | 324/233 |
| 5,642,050 A | * | 6/1997 | Shoemaker | 324/329 |
| 5,654,638 A | * | 8/1997 | Shoemaker | 324/329 |
| 5,994,897 A | * | 11/1999 | King | 324/236 |
| 6,636,827 B2 | * | 10/2003 | Sakagami | 702/193 |
| 6,816,794 B2 | * | 11/2004 | Alvi | 702/35 |
| 7,385,392 B2 | * | 6/2008 | Schlicker et al. | 324/242 |
| 7,432,715 B2 | * | 10/2008 | Stamatescu | 324/345 |
| 7,679,377 B2 | * | 3/2010 | Schroder | 324/664 |
| 2002/0163333 A1 | * | 11/2002 | Schlicker et al. | 324/242 |
| 2003/0107371 A1 | * | 6/2003 | Engdahl et al. | 324/233 |
| 2005/0127908 A1 | * | 6/2005 | Schlicker et al. | 324/240 |
| 2005/0165297 A1 | * | 7/2005 | Anderson et al. | 600/410 |
| 2010/0148761 A1 | * | 6/2010 | Moskalenko | 324/202 |

* cited by examiner

*Primary Examiner* — Timothy J Dole
*Assistant Examiner* — Benjamin M Baldridge
(74) *Attorney, Agent, or Firm* — David George Johnson

(57) ABSTRACT

A metal detector used for identifying contaminants in packages on a conveyor. The detector includes coils a search head and an analog to digital converter generating a reactive signal and a resistive signal in response to the presence of a contaminant. During a learning mode a sample product passes through the metal detector providing a representative product effect signal which is stored by the reactive learn memory and the resistive learn memory. The learn memory values provide a reference value subtracted from each product signal during a normal production cycle, canceling the product effect caused by contaminants in individual packages. The product effect is monitored during successive cycles composed of a series of packages undergoing normal inspection by the metal detector. A tracking processor averages the product effect signal produced by the individual packages and continuously updates a product effect trend signal that is subtracted from each product signal.

19 Claims, 5 Drawing Sheets

APPARATUS AND METHOD FOR AUTOMATIC PRODUCT EFFECT COMPENSATION IN RADIO FREQUENCY METAL DETECTORS

BACKGROUND OF THE INVENTION

1. Field of Invention

This invention pertains generally to the field of radio frequency metal detectors, and more particularly to the calibration of such a device.

2. Description of Prior Art

Metal detectors are used in the food processing industry, for example, to detect contaminants within a product. The unwanted material may include very small metallic particles having differing compositions. As seen in FIG. 2, the typical metal detector is housed in an enclosure 26 containing a longitudinal aperture 25 through which the product under test 23 is transported, usually by means of a conveyor belt, in the direction of arrow 24. The metal detector includes a radio frequency transducer or oscillator that radiates a magnetic field by means of some arrangement of coils that serve as a radio frequency antenna. An example of such a metal detector operating in the radio frequency range is disclosed in U.S. Pat. No. 5,994,897, entitled FREQUENCY OPTIMIZING METAL DETECTOR, issued on Nov. 30, 1999 to King.

The typical metal detector enclosure 26 includes both radiating and receiving coils formed to surround the aperture 25 through which the product travels. The oscillator coil is a continuous wire loop formed within the search head. The oscillator coil surrounds the aperture 25 and receives radio frequency excitation from an oscillator circuit. The enclosure 26 also includes an input coil connected to produce a zero input signal when no metal is present.

A disturbance in the radiated magnetic field is sensed by the input coil and processed in order to detect a metal contaminant within the product passing through the detector aperture. Modern digital signal processing techniques resolve the input signal into two signal components, one component being resistive and the other signal component being reactive. FIG. 1 depicts a typical signal processing scheme used in such a metal detector. The coils 1 are connected to the search head 2 that contains a radio frequency transmitter and receiver. When the coils 1 receive an electromagnetic signal the search head 2 divides the received signal into a reactive (X) component 11 and a purely resistive component 12. The signals 11 and 12 are in an analog form and so are forwarded to the analog to digital (A/D) converter 3 where the signal 11 is converted into a digital reactive component signal 13 and a digital resistive component signal 14. An example of a metal detector using digital signal processing techniques is disclosed in U.S. Pat. No. 7,432,715, entitled METHOD AND APPARATUS FOR METAL DETECTION EMPLOYING DIGITAL SIGNAL PROCESSING, issued on Oct. 7, 2008 to Stamatescu.

A nonzero input coil signal is due to either mechanical imbalances in the construction of the search head, inherent electrical changes in the circuitry such as frequency drift, metal being introduced into the aperture, or the effect of the product itself. The "product effect" is caused by the product passing through the aperture and is due primarily to electrical conduction via salt water within the product, the electrical conduction causing large magnitude resistive signals and relatively smaller reactive signals.

Calibration of a metal detector including compensation for the effect of the product is usually accomplished by the user of the detector. This process is dependent on operator skill and experience, and results in inconsistent results between different operators using the same machine. An example of a manually operated interactive metal detection calibration process is disclosed in U.S. Pat. No. 6,816,794, entitled APPARATUS AND METHOD FOR DETECTING CONTAMINATION OF OBJECT BY A METAL, issued on Nov. 9, 2004 to Alvi.

An attempt to directly address the effect of the product is disclosed in U.S. Pat. No. 6,636,827, entitled FOREIGN MATTER DETECTOR AND FOREIGN MATTER DETECTING SYSTEM, which was issued to Sakagami on Oct. 21, 2003. The Sakagami system relies on a library of stored product effect parameters that are manually selected by the equipment operator in order to reduce the sensitivity of the metal detector to the effect of the product.

A related patent is U.S. Pat. No. 5,045,789, DETECTOR FOR DETECTING FOREIGN MATTER IN OBJECT BY USING DISCRIMINANT ELECTROMAGNETIC PARAMETERS, issued on Sep. 3, 1991 to Inoue, et al, which discloses the concept of defining a set of parameters or values which define the detecting envelope, and thus the border between an acceptable product and one containing metal.

U.S. Pat. No. 4,719,421, entitled METAL DETECTOR FOR DETECTING PRODUCT IMPURITIES, issued on Jan. 12, 1988 to Kerr discloses the use of an adjustable phase shifter (element 10 in FIG. 2). The phase shifter is adjusted to provide a null or linear output in response to product variations that might otherwise erroneously indicate the presence of metal. More specifically, if a nonlinear output is produced more than a given number of times in succession, thereby indicating that the nonlinearity is characteristic of that particular product, then the phase shifter is adjusted to produce a linear output.

There are numerous disadvantages to the metal calibration methods just described. In general, the operator of the metal detector does not have a clear understanding of the concept and function of the metal detection process. This lack of understanding leads to misuse of detection calibration controls and necessarily to a reduction in metal detector sensitivity due to improper settings of the metal detector system. A need therefore exists to employ a method of metal detector product effect compensation which permits substantially all product effect corrections to be performed automatically by the metal detector.

SUMMARY OF THE INVENTION

The current invention relates to improvements in compensating for the effect of a product when the product itself is undergoing inspection by a metal detector by using a time synchronized digital subtraction technique. The present invention improves the simultaneous sensitivity of the detector for metals of different groups by eliminating the need to eliminate signals having a phase component that is also a characteristic phase produced by the product under test. A second aspect of the present invention includes the tracking of trends or changes in the product effect characteristic during the normal flow of multiple products through the metal detector. A change in the average effect generated by the products being examined is used to modify the reference signal employed by the metal detector when the time synchronized digital subtraction technique is active.

DETAILED DESCRIPTION OF THE PREFERRED EMBODIMENTS

Figure 1:
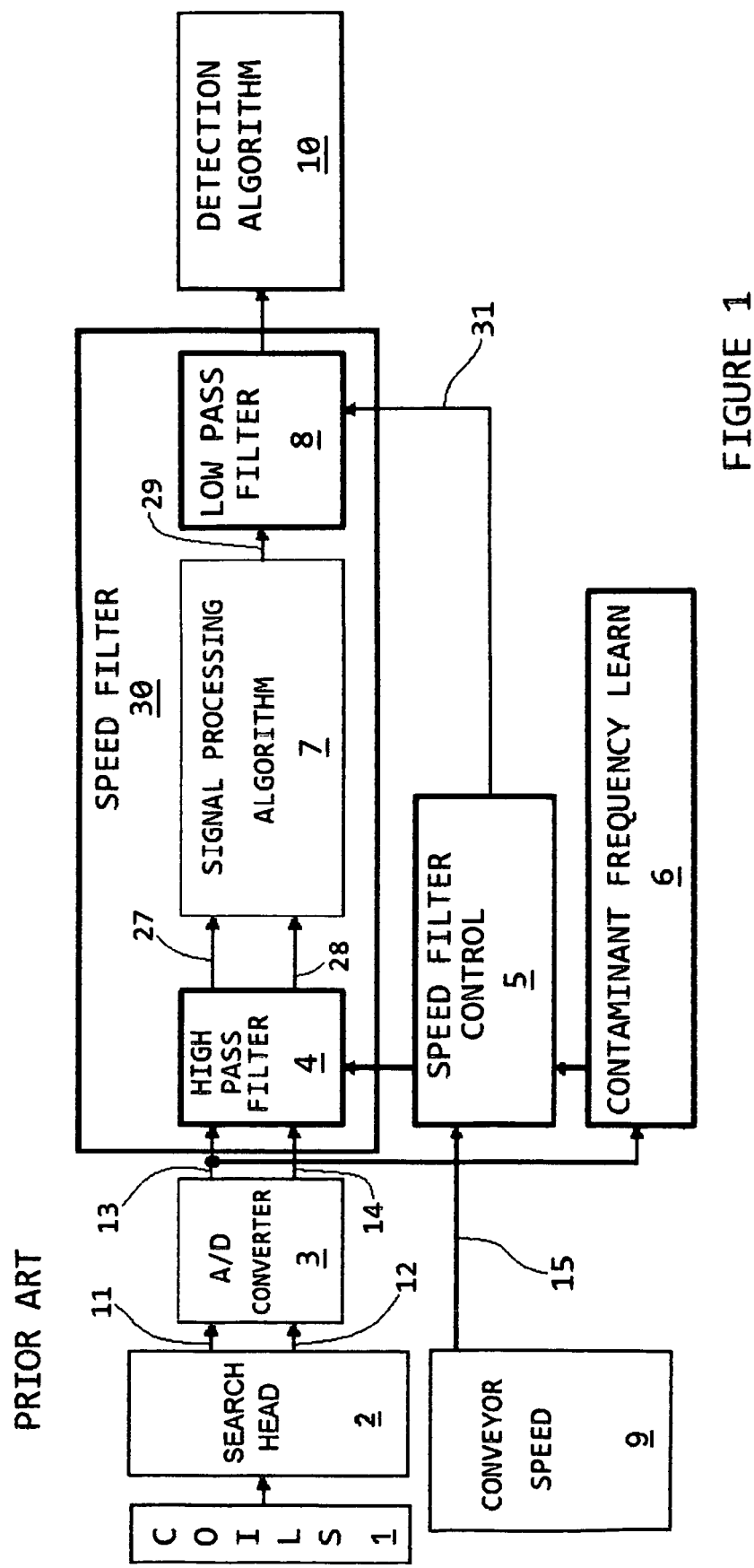
FIG. 1 is a block diagram of the prior art signal processing scheme of a metal detector.
Figure 2:
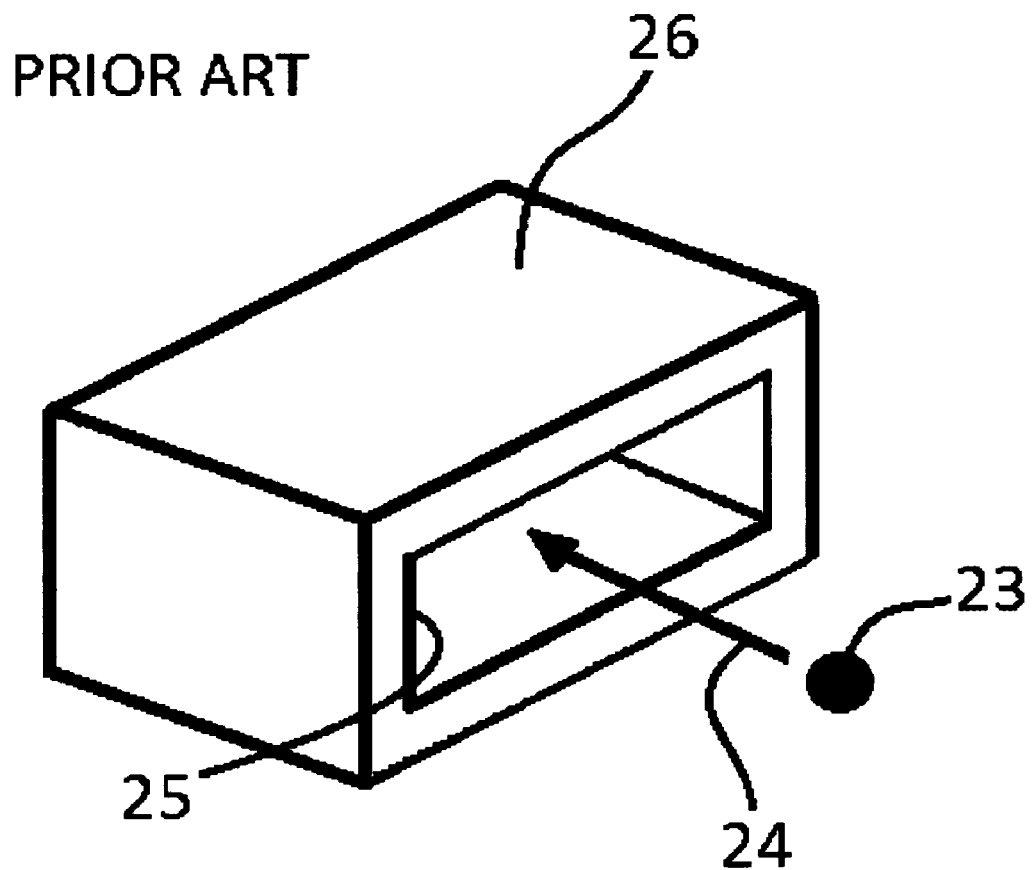
FIG. 2 is a perspective view of an enclosure and aperture arrangement used in the metal detector depicted in FIG. 1.
Figure 3:
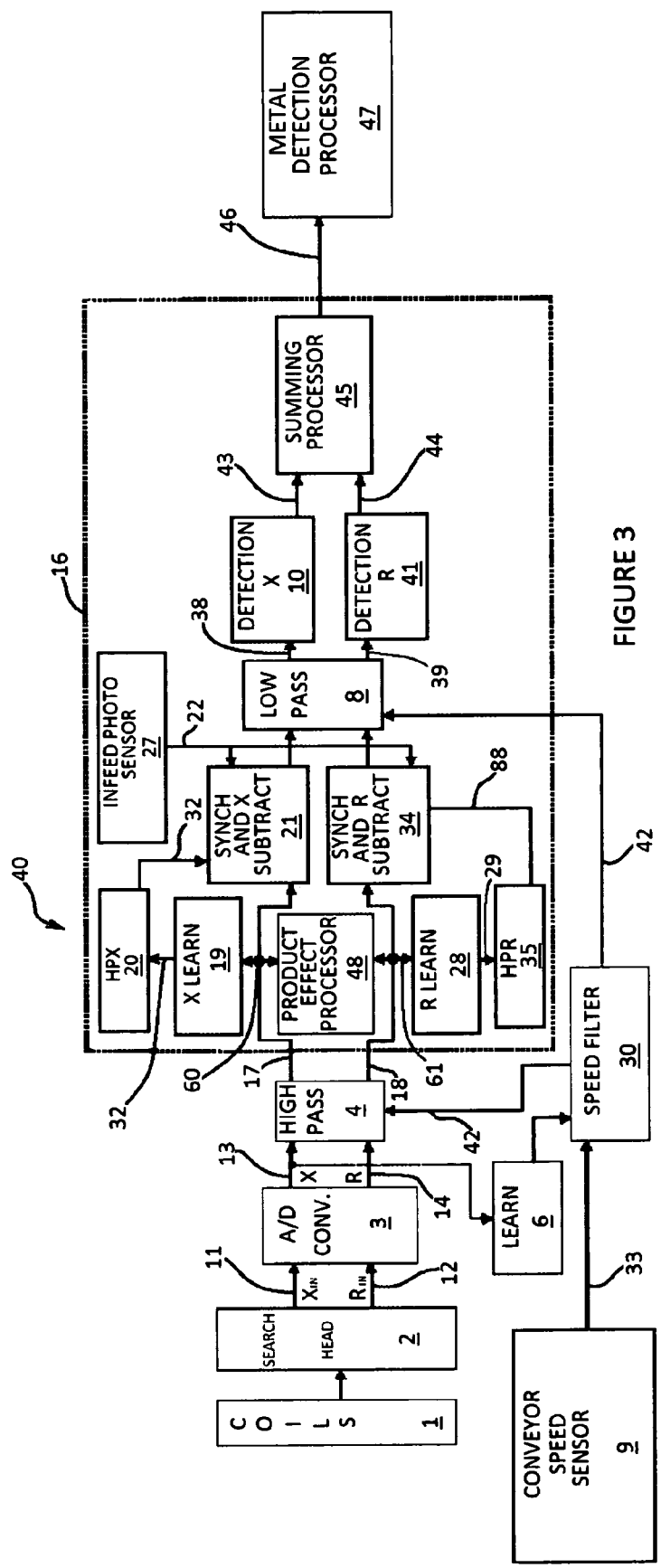
FIG. 3 is a block diagram of the metal detector signal processing protocol of the present invention.

Referring to FIG. 3, a block diagram of a metal detector constructed according to the principles of the present invention is shown generally at 40. The signals 11 and 12 generated by the search head 2 is processed by the analog to digital converter 3. The resultant digital reactive component signal 13 and resistive component signal 14 are forwarded to a high pass filter 4 for further signal processing. The metal detector 40 includes the capability to measure the instantaneous conveyor speed 33 via conveyor speed sensor 9, the conveyor speed 33 being substantially equal to the speed of any article being introduced into the region of the detector coils 1. The metal detector 40 includes a speed filter 30, which contains a signal processing hardware or software that provides the necessary information to the metal detection algorithm processors 10 and 41 which are capable of determining the presence or absence of a contaminant such as metal.

The speed filter 30 receives data from the conveyor speed sensor 9 in order to provide a correction or adjustment signal to the high pass filter 4 and the low pass filter 8 depending on the value of certain variables including the conveyor speed 33. The speed filter 30 also receives data derived from the digitized reactive output signal 13, thereby providing a basis for the speed filter to correlate the frequency response of the search head 2 with the conveyor speed 9. For each conveyor speed 9, an optimum frequency exists at which the signal processing algorithm best detects the presence of a contaminant within the region of the coils 1. In order to determine the optimum frequency, contaminant frequency learn processor 6 receives the signal 13 that is derived from the data produced by the search head 2 and correlates the signal 13 with other constant parameters including the physical configuration of the coils 1, and the physical dimensions of the case housing the metal detector 40 and the conveyor speed 9 which is a variable that is dependent on the nature of the specific type of product being introduced into the region of the coils 1.

The speed fitter correction data 42 is forwarded to both the high pass filter 4 and the low pass filter 8. The high pass filter 4 receives and filters both the reactive component input signal 13 and resistive component input signal 14 received from the analog to digital converter 3. The high pass filter 4 generates a filtered reactive component output signal 17 and a filtered resistive component output signal 18. The filtered data enters the product effect compensation section 16 of the metal detector 40, which includes a sample product effect learn mode that is activated when a sample product having nominal characteristics is introduced into and examined by the search head 2. When such a nominal sample product is being inspected, the filtered reactive component output signals 17 are forwarded to reactive component learn memory 19 where the nominal reactive component output signal is stored as reactive reference data 32. When the metal detector 40 is functioning in a production mode and thereby continuously processing numerous products in a serial fashion, the reactive reference data 32 that is stored in the reactive component learn memory is forwarded to the reactive effect reference processor 20.

As each product is inspected during the production mode, the reactive component residing in the reactive effect reference processor is sent to the reactive component synchronization processor 21 and subtracted from the reactive signal produced by the specific product under test. The reactive component synchronization processor 21 receives a signal 22 from the infeed photo sensor 27 in order to initiate subtraction of the reactive reference data 32 from the signal actually being generated in response to a product under inspection which can occur only when such a product is present.

When a nominal sample product is being inspected, the filtered resistive component output signal 18 is simultaneously forwarded to the resistive component learn memory 28 where the nominal resistive component output signal is stored as resistive reference data 29. When the metal detector 40 is functioning in a production mode and continuously processing numerous products in a serial fashion, the resistive reference data 29 that is stored in the resistive component learn memory is forwarded to the resistive effect reference processor 35.

As each product is being inspected during the production mode, the resistive component data 29 residing in the resistive effect reference processor 35 is sent to the resistive component synchronization processor 34 via path 88 and subtracted from the resistive signal produced by the specific product under test. The resistive component synchronization processor 34 also receives a signal 22 from the infeed photo sensor 27 in order to subtract the resistive reference data 32 from the signal actually being generated in response to a product under inspection which occurs only when such a product is present in the region of the coils 1.

The reactive component synchronization processor 21 generates an output signal 36 that represents the difference signal between the product under test and the reactive reference product effect signal 32. Similarly, the resistive component synchronization processor 34 generates an output signal 37 that represents the difference between the product actually undergoing inspection and the resistive reference product effect signal 29. Both of these difference signals 36 and 37 are forwarded to the low pass filter 8, thereby creating a filtered reactive output signal 38 and a filtered resistive output signal 39.

The filtered reactive output signal 38 is forwarded to reactive component detection algorithm processor 10 which generates a reactive detection output signal 43. Similarly, the filtered resistive output signal 39 is forwarded to the resistive component detection algorithm 41 to create a resistive detection output signal 44. Summing processor 45 adds the two component detection signals 43 and 44 to create a single output signal 46 that serves as the input to the metal detection processor 47.

Figure 4:
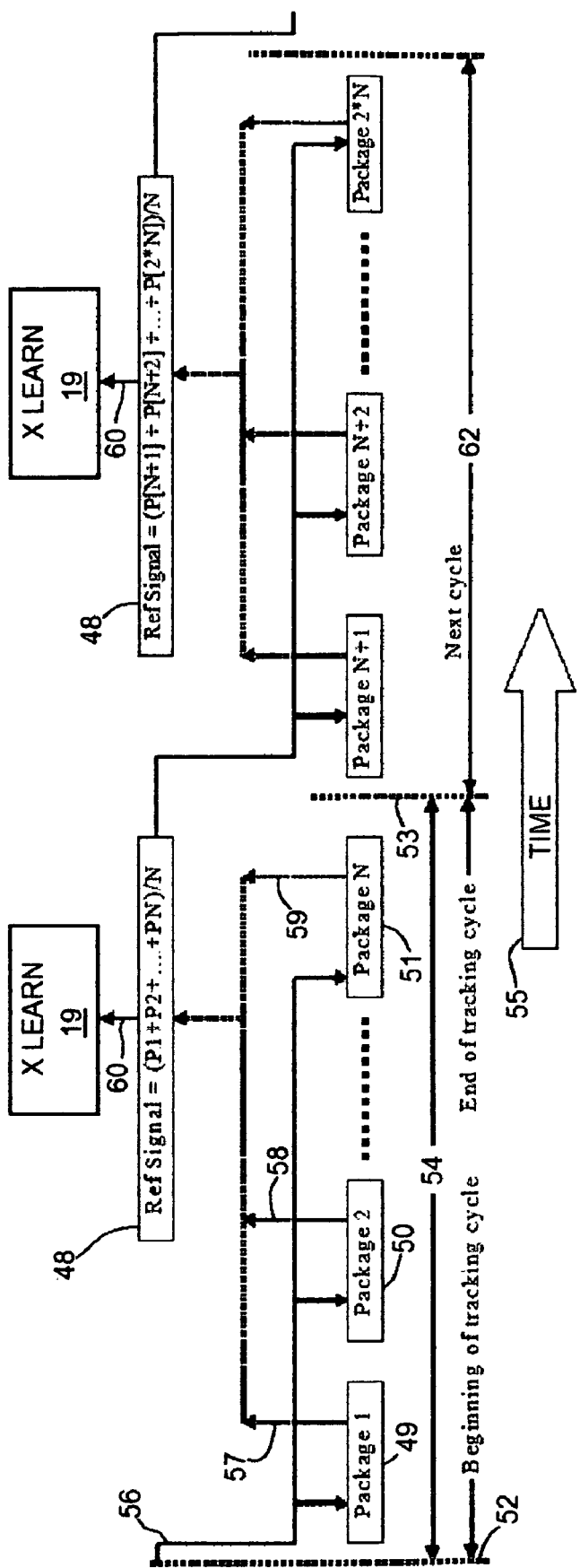
FIG. 4 is a timing diagram depicting the product effect tracking feature depicted in FIG. 3.

As the flow of products through the metal detector 40, the trend of the individual product effect signals is monitored by tracking processor 48 which is able modify the reference signals 29 and 32 as necessary. Referring also to FIG. 4, the product effect tracking function performed by tracking processor 48 may be better understood. Only the reactive component signal tracking function is depicted in FIG. 4, with the resistive component tracking being accomplished in a substantially similar manner.

Each series of packages, composed of packages 49, 50 and 51, for example, triggers the beginning 52 and end 53 of a product tracking cycle 54. The elapsed time since the beginning 56 (time=0) of the product inspection period is increasing in the direction of arrow 55. Since each package generates its own individual product effect signal, the first package 49 generates a first product effect signal 57, the second package 50 generates a second product effect signal 58 and the third package 51 generates a third product effect signal 59. Each of the product effect signals 57, 58 and 59 is forwarded to the tracking processor 48 which generates a reactive trend signal 60 as well as a resistive trend signal 61. The tracking processor 48 receives each of the individual product effect signals 57, 58 and 59 and divides the sum of the signals by three, thereby creating a reactive trend signal 60 which is the average of the individual product effect signals of all of the packages 49, 50 and 51 that have been monitored during the cycle 54. The reactive trend signal 60 is sent to the reactive component learn memory 19 where it is compared to the original reference signal generated by a test package prior to the beginning of any product tracking cycle. Only packages not having a metal contaminant as determined by the metal detection processor 47 are used to determine product effect trends. The original reference signal is subtracted from the reactive trend signal and then forwarded for use by the reactive component reference processor 20 at the end of the monitoring cycle 54. After monitoring cycle 54 is completed, the next cycle 62 begins.

The number of packages per product tracking cycle is not limited to three. In the general case, the number of packages monitored during each product tracking cycle is N, and the reactive trend signal 60 is expressed as $$R=(P_1+P_2+\ldots+P_N)/N, \text{ where}$$

R is the average inherent product effect characteristic,
P is a product effect of each individual package being inspected and
N is the total number of packages inspected.

Figure 5:
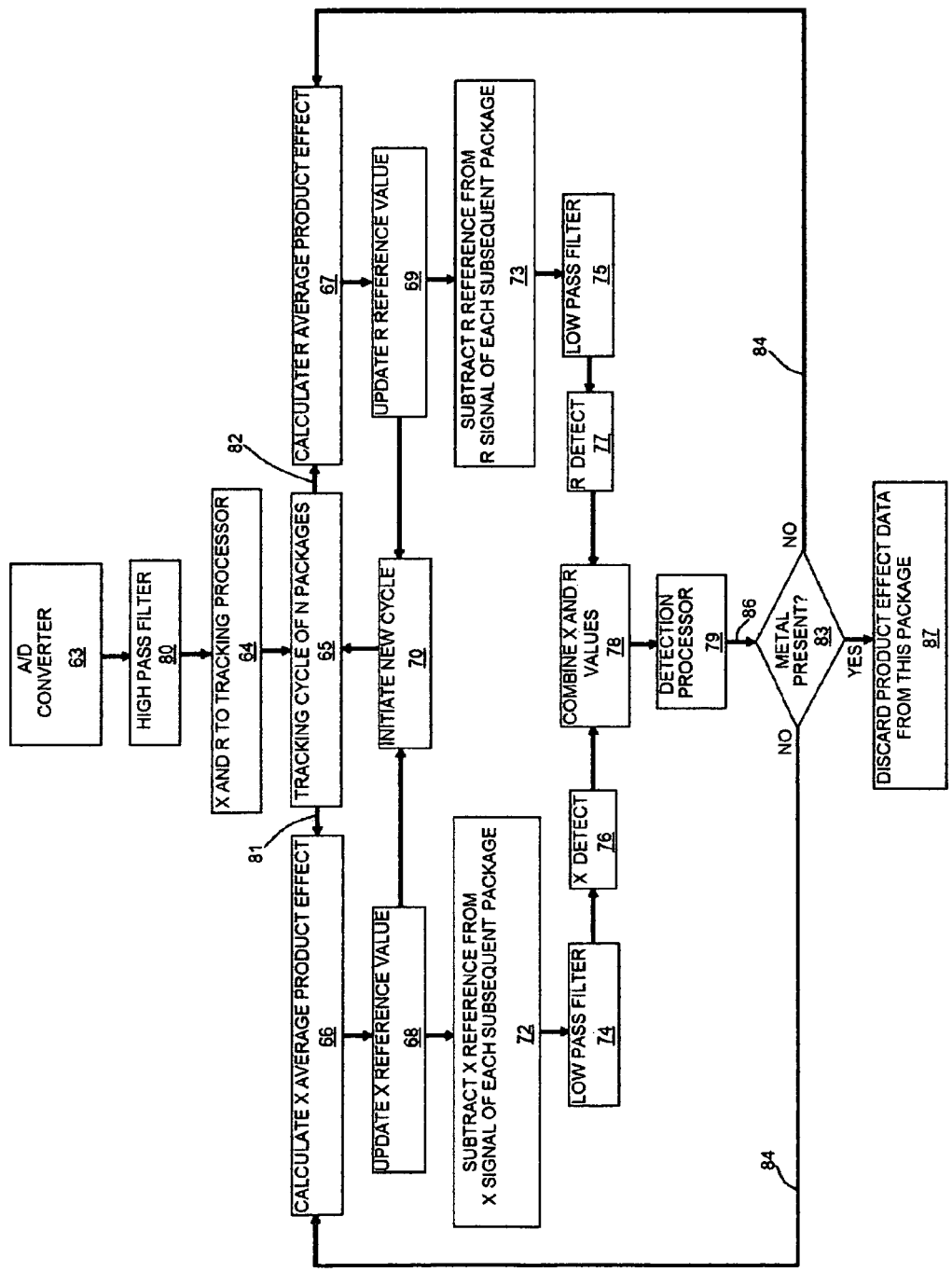
FIG. 5 is a flow chart showing the signal processing protocol utilized by the product effect tracking feature depicted in FIG. 4.

As best seen in FIG. 5, when utilizing the product effect tracking feature the initial step 63 is to convert the raw analog data 11 and 12 into a digitized reactive component 13 and a digitized resistive component 14, both of which are then processed by the high pass filter 4 at step 80. The filtered component signals 17 and 18 are then sent at step 64 to the tracking processor 48, which performs a tracking cycle at step 65 that includes a predetermined number N of packages, such as packages 49, 50 and 51. The tracking processor 48 functions simultaneously on both a reactive component calculation path 81 and a resistive component calculation path 82. Each filtered reactive signal component 17 in any given tracking cycle is stored and averaged at step 66, with the averaged value being used to update the reactive product effect reference signal at step 68. Once the reference signal update has occurred a new cycle is initiated at step 70. The averaged reactive value calculated at step 68 is subtracted at step 72 from the reactive signal component 17 generated by each individual product undergoing inspection, with the difference value being filtered by the low pass filter 8 at step 74. The filtered signal produced at step 74 is then processed by the reactive detection algorithm processor 10 at step 76.

Similarly, each filtered resistive signal component 18 in each tracking cycle is stored and averaged at step 67, with the averaged value being used to update the resistive product effect reference signal at step 69. Once the resistive reference signal update has occurred a new cycle is initiated at step 70. The averaged resistive value calculated at step 69 is subtracted at step 73 from the resistive signal component 18 generated by each individual product undergoing inspection, with the difference value being filtered by the low pass filter 8 at step 75. The filtered signal produced at step 75 is then processed by the resistive detection algorithm processor 41 at step 77. The two detection signals 43 and 44 representing the reactive and resistive signal components, respectively, are added at step 78 and forwarded to the metal detection processor 47 at step 79. The output signal 86 of the metal detection processor 47 is forwarded to logical IF processor 83 which determines if a metal contaminant was detected in the inspected product inspected. If metal is detected, path 85 sends the product effect data for that package to be discarded at step 87. If no metal is detected, path 84 causes the product effect data for that package to be retained for the product effect calculation of step 66.

The foregoing improvements embodied in the present invention are by way of example only. For example, the product effect tracking feature just described may be omitted or used selectively in response to the expected variation in product effect for successive package during a given inspection period. Those skilled in the metal detecting field will appreciate that the foregoing features may be modified as appropriate for various specific applications without departing from the scope of the claims.

I claim:

1. A metal detector adapted to transport a product through a region intersecting an electromagnetic field, comprising:
    (a) at least one coil residing within the electromagnetic field, the coil generating a signal in response to a disturbance of the electromagnetic field;
    (b) an infeed sensor, the infeed sensor detecting entry of each product into the region intersecting the electromagnetic field and generating an infeed output signal in response thereto;
    (c) an analog to digital converter, the analog to digital converter receiving the signal and generating a plurality of output signals, comprising;
        i) a first output signal, the first output signal representing a reactive component of the signal generated by the coil; and
        ii) a second output signal, the second output signal representing a resistive component of the signal generated by the coil;
    (d) a reactive component learn memory, the reactive component learn memory receiving the first output signal and generating a reactive component reference signal in response thereto; and
    (e) a reactive component synchronization processor, the reactive component synchronization processor receiving the infeed sensor output signal and the reactive component reference signal, the reactive component synchronization processor subtracting the reactive component reference signal from a reactive signal generated by a product being inspected by the metal detector so as to generate a subtracted reactive component signal having a substantially reduced product effect.

2. The metal detector according to claim 1, further comprising a resistive component learn memory, the resistive component learn memory receiving the second output signal and generating a resistive component reference signal in response thereto.

3. The metal detector according to claim 2, further comprising a resistive component synchronization processor, the resistive component synchronization processor receiving the infeed sensor output signal and the resistive component reference signal, the resistive component synchronization processor subtracting the resistive component reference signal from a resistive signal generated by a product being inspected by the metal detector so as to generate a subtracted resistive component signal having a substantially reduced product effect.

4. The metal detector according to claim 3, further comprising a first metal detection algorithm processor, the first metal detection algorithm processor receiving the subtracted reactive component signal and generating a first detection signal having a characteristic related to a level of metal contamination within a product being inspected by the metal detector.

5. The metal detector according to claim 4, further comprising a second metal detection algorithm processor, the second metal detection algorithm processor receiving the subtracted resistive component signal and generating a second detection signal having a characteristic related to a level of metal contamination within a product being inspected by the metal detector.

6. The metal detector according to claim 5, further comprising a summing processor, the summing processor being interconnected to the first and second metal detection algorithm processors, the summing processor adding the first and second detection signals together to generate a composite output signal.

7. The metal detector according to claim 6, further comprising a metal detection processor, the metal detection processor being interconnected to the summing processor and receiving the composite output signal from the summing processor, the summing processor generating an output indicative of a metal content of a product being inspected by the metal detector.

8. The metal detector of claim 7, further comprising a tracking processor, the tracking processor receiving a signal derived from the analog to digital converter, the tracking processor storing successive reactive component signals attributable to successive products inspected by the metal detector.

9. The metal detector of claim 8, wherein the tracking processor is storing successive resistive component signals attributable to successive products inspected by the metal detector.

10. The metal detector of claim 9, wherein the tracking processor generates a tracking processor reactive component output signal that is substantially equal to an average of reactive component reference signals received by the tracking processor during a predetermined period.

11. The metal detector of claim 10, wherein the tracking processor generates a tracking processor resistive component output signal that is substantially equal to an average of resistive component reference signals received by the tracking processor during a predetermined period.

12. The metal detector of claim 11, wherein the tracking processor reactive component output signal is forwarded to the reactive component learn memory, the tracking processor reactive component output signal being utilized as the reactive component reference signal when received by the reactive component learn memory.

13. The metal detector of claim 11, wherein the tracking processor resistive component output signal is forwarded to the resistive component learn memory, the tracking processor resistive component output signal being utilized as the resistive component reference signal after being received by the resistive component learn memory.

14. The metal detector of claim 11, wherein the average value for the digital resistive component signal and the digital reactive component signal is subtracted from a previous value of average value of digital resistive component signals and digital reactive component signals to create updated value for a digital resistive component signal and a digital reactive component signal due to the product effect.

15. The metal detector of claim 14, wherein the updated value of the digital resistive component signal and the digital reactive component signal is used as a reference signal that is valid for subsequent operations performed by the metal detector.

16. A metal detector providing cancellation of a product effect, comprising:
    (a) transmitting and receiving coils capable of generating and detecting an electromagnetic field, respectively;
    (b) a search head housing the transmitting and receiving coils in a fixed configuration, the search head providing an analog resistive component signal and an analog reactive component signal;
    (c) an analog to digital converter interconnected to the search head for converting analog signals generated in response to a disturbance of the electromagnetic field into digital signals, the analog to digital converter providing a digital resistive component signal and a digital reactive component signal;
    (d) a means for transporting a product undergoing inspection through the electromagnetic field;
    (e) a high pass filter, the high pass filter being electrically interconnected to the analog to digital converter, the high pass filter passing a relatively narrower range of frequencies contained within the digital resistive component signal and a digital reactive component signal digital signals generated by the analog to digital converter to a tracking processor, wherein the tracking processor stores a number of digital resistive component signals and digital reactive component signals and generates an average value for the digital resistive component signal and the digital reactive component signal.

17. A method of diminishing a product effect in a metal detector, comprising the steps of:
    (a) radiating an electromagnetic field into an aperture of the metal detector;
    (b) receiving the electromagnetic field, thereby producing a received signal;
    (c) introducing a representative sample product into the aperture while the electromagnetic field is present within the aperture;
    (d) separating the received signal into a resistive component and a reactive component;
    (e) calculating the average inherent product effect characteristics of products under test according to the formula $R=(P1+P2+\ldots+PN)/N$, where R is the average inherent product effect characteristic,
    P is a product effect of each individual package being inspected and
    N is the total number of packages inspected;
    (f) storing inherent product effect characteristics of the representative sample product, the inherent characteristics being constants;
    (g) subtracting the inherent product effect characteristics of the representative sample product from signals received by subsequent products undergoing inspection by the metal detector.

18. The method of claim 17, further comprising the step of altering the inherent product effect characteristics of the representative sample product by substituting the average inherent product effect characteristic calculated from the product effect signal received from subsequent products undergoing inspection by the metal detector.

19. The method of claim 17, further comprising the step of determining the average inherent product characteristic of products undergoing inspection in a substantially continuous cyclical fashion throughout an inspection period performed by the metal detector.

* * * * *